(12) United States Patent
Reslow et al.

(10) Patent No.: US 6,936,278 B2
(45) Date of Patent: Aug. 30, 2005

(54) MICROPARTICLES

(75) Inventors: Mats Reslow, Lund (SE); Monica Jönsson, Bara (SE); Karin Larsson, Torna Hällestad (SE); Timo Laakso, Campton (GB)

(73) Assignee: Jagotec AG, Muttenz (CH)

( * ) Notice: Subject to any disclaimer, the term of this patent is extended or adjusted under 35 U.S.C. 154(b) by 249 days.

(21) Appl. No.: 10/162,674

(22) Filed: Jun. 6, 2002

(65) Prior Publication Data

US 2003/0180371 A1 Sep. 25, 2003

(30) Foreign Application Priority Data

Mar. 21, 2002 (SE) ................................. 0200873
May 30, 2002 (SE) ................................. 0201599

(51) Int. Cl.[7] ........................... A61F 2/00; A61F 13/00; A61K 9/14; A61K 9/16; A61K 9/50
(52) U.S. Cl. ........................ 424/489; 424/422; 424/423; 424/424; 424/425; 424/490; 424/497; 424/499; 424/501
(58) Field of Search ................................. 424/422, 423, 424/424, 425, 489, 490, 497, 499, 501

(56) References Cited

U.S. PATENT DOCUMENTS

| 3,691,090 A | 9/1972 | Kitajima et al. |
| 3,737,337 A | 6/1973 | Schnoring et al. |

(Continued)

FOREIGN PATENT DOCUMENTS

| EP | 0 213 303 A2 | 3/1987 |
| EP | 0 245 820 | * 11/1987 |
| EP | 0 540 582 B1 | 8/1994 |
| EP | 0 688 429 B1 | 2/1998 |
| EP | 0 330 180 B2 | 3/1999 |
| JP | 11302156 | 11/1999 |
| WO | WO 90/13780 A1 | 11/1990 |
| WO | WO 93/21008 A1 | 10/1993 |
| WO | WO 94/27718 A1 | * 12/1994 |
| WO | WO 94/27718 | 12/1994 |
| WO | WO 94/12158 A1 | 6/1995 |
| WO | WO 96/10042 A1 | 4/1996 |
| WO | WO 97/14408 A1 | 4/1997 |
| WO | WO 99/00425 A1 | 1/1999 |
| WO | WO 99/20253 A1 | 4/1999 |
| WO | WO 02/39985 | 5/2002 |
| WO | WO 02/39985 A1 | * 5/2002 |

OTHER PUBLICATIONS

US 5,849,884, 12/1998, Woiszwillo et al. (withdrawn)

(Continued)

Primary Examiner—Thurman K. Page
Assistant Examiner—S. Tran
(74) Attorney, Agent, or Firm—Mintz, Levin, Cohn, Ferris, Glovsky and Popeo, P.C.

(57) ABSTRACT

A process for producing microparticles, in which an aqueous solution of purified amylopectin-based starch of reduced molecular weight is prepared, the solution is combined with biologically active substance, an emulsion of starch droplets is formed in an outer phase of polymer solution, the starch droplets are made to gel, the gelled starch particles are dried, and a release-controlling shell is optionally applied to the particles, wherein at least one buffer substance having the ability of keeping the pH of the produced microparticles above 3 if exposing the microparticles to an aqueous environment is added at any stage during the process.

Microparticles which essentially consist of said starch, have an amino acid content of less than 50 $\mu$g and have no covalent chemical cross-linking and which have the aktivity of keeping the pH above 3 if exposed to a aqueous environment.

34 Claims, 1 Drawing Sheet

U.S. PATENT DOCUMENTS

| | | | | |
|---|---|---|---|---|
| 3,881,991 | A | | 5/1975 | Kurimotor et al. |
| 4,389,330 | A | | 6/1983 | Tice et al. |
| 4,393,202 | A | * | 7/1983 | Breuninger ................. 536/102 |
| 4,713,249 | A | | 12/1987 | Schröder |
| 5,279,658 | A | * | 1/1994 | Aung ...................... 106/126.1 |
| 5,378,491 | A | * | 1/1995 | Stanley et al. .............. 426/661 |
| 5,407,609 | A | | 4/1995 | Tice et al. |
| 5,455,342 | A | | 10/1995 | Redding, Jr. |
| 5,470,582 | A | | 11/1995 | Supersaxo et al. |
| 5,578,709 | A | | 11/1996 | Woiszwillo et al. |
| 5,622,657 | A | | 4/1997 | Takada et al. |
| 5,654,010 | A | | 8/1997 | Johnson et al. |
| 5,667,808 | A | | 9/1997 | Johnson et al. |
| 5,753,234 | A | | 5/1998 | Lee et al. |
| 5,776,885 | A | | 7/1998 | Orsolini et al. |
| 5,792,477 | A | | 8/1998 | Rickey et al. |
| 5,981,719 | A | | 11/1999 | Woiszwillo et al. |
| 5,997,945 | A | * | 12/1999 | Shasha et al. ............ 427/213.3 |
| 6,123,920 | A | * | 9/2000 | Gunther et al. .......... 424/9.322 |
| 6,340,527 | B1 | * | 1/2002 | Van Soest et al. ....... 428/402.2 |
| 6,602,994 | B1 | * | 8/2003 | Cash et al. .................... 536/30 |
| 6,616,948 | B2 | * | 9/2003 | Gustavsson et al. ........ 424/497 |
| 6,692,770 | B2 | * | 2/2004 | Gustavsson et al. ........ 424/493 |
| 6,706,288 | B2 | * | 3/2004 | Gustavsson et al. ........ 424/497 |
| 2002/0009493 | A1 | | 1/2002 | Schwendeman et al. |

OTHER PUBLICATIONS

Stenekes et al., "The Preparation of Dextran Microspheres in an All–Aqueous System: Effect of the Formulation Parameters on Practivel Characteristics," Pharmaceutical Research, vol. 15, No. 4, pp. 557–561 (1998).*

Stjarnkvist et al., "Biodegradable Microspheres XII: Properties of the Crosslinking Chains in Polyacryl Starch Microparticles", Journal of Pharmaceutical Sciences, vol. 78, No. 1, pp. 52–56, (1969).*

Artursson et al., "Characterization of Polyacryl Starch Microparticles as Carriers for Proteins and Drugs," Journal of Pharmaceutical Sciences, vol. 73, No. 11, pp. 1507–1513, (1984).

Franssen et al., "A Novel Preparation Method for Polymeric Microparticles without the Use of Organic Solvents," International Journal of Pharmaceutics, vol. 168, pp. 1–7 (1998).

Fu et al., "Visual Evidence of Acidic Environment Within Degrading Poly(lactic–co–glycolic acid) (PLGA) Microspheres" Pharmaceutical Research, vol. 17, No. 1, pp. 100–106 (2000).

Laakso et al., "Biodegradable Microspheres IV: Factors Affecting the Distribution and Degradation of Polyacryl Starch Microparticles," Journal of Pharmaceutical Sciences, vol. 75, No. 10, pp. 962–967 (1986).

Laakso et al., "Biodegradable Microspheres X: Some Properties of Polyacryl Starch Microparticles Prepared from Acrylic Acid–Esterified Starch," Journal of Pharmaceutical Sciences, vol. 76, No. 12, pp. 935–939 (1987).

Schröder, "Crystallized Carbohydrate Spheres as a Slow Release Matrix for Biologically Active Substances," Biomaterials, vol. 5, pp. 100–104 (1984).

Schröder, "Crystallized Carbohydrate Spheres for Slow Release and Targeting," Enzymology, vol. 112, No. 9, pp. 116–128 (1985).

Stenekes et al., "The Preparation of Dextran Microspheres in an All–Aqueous System: Effect of the Formulation Parameters on Particle Characteristics," Pharmaceutical Research, vol. 15, No. 4 pp. 557–561 (1998).

Stjärnkvist et al., "Biodegradable Microspheres XIII: Properties of the Crosslinking Chains in Polyacryl Starch Microparticles," Journal of Pharmaceutical Sciences, vol. 78, No. 1, pp. 52–56 (1989).

Agersø et al., "Plasma Concentration of hGH and anti–hGH Antibodies After Subcutaneous Administration of hGH for 3 Weeks to Immunosuppressed Pigs," J. Pharmacol Toxicol No. 41 pp. 1–8 (1999).

Johnson et al., "A Month–Long effect From a Single Injection of Microencapsulated Human Growth Hormone," Nature Medicine, vol. 2, No. 7 pp. 795–799 (1996).

Putney, "Encapsulation of Proteins for Improved Delivery," Current Opinion in Chemical Biology, Nol. 2, pp. 548–552 (1998).

"Clean Package Insert," Nutropin Depot (somatropin(rDNA origin) for injectable suspension), Genentech, Inc., 1 DNA Way, South San Francisco, CA 940–4990, pp. 1–6 (Dec. 13, 1999).

"Formation and Isolation of Spherical Fine Protein Microparticles Through Lyophilization of Protein—Poly(ethylene glycol) Aqueous Mixture", Takahiro Morita et al., Pharmaceutical Research, vol. 17, 11, 2000, pp. 1367 to 1373.

Protein encapsulation into biodegradable microspheres by a novel S/O/W encapsulation method using poly(ethylene glycol) as a protein micronization adjuvant, Takahiro Morita et al., Journal of Controlled Release, 69 (2000) pp. 435–444.

Schwendeman et al. "Stability of Encapsulated Substances in Poly (Lactide–co–Glycolide) Delivery Systems", Handbook of Pharmaceutical Controlled Release Technology, New York, Marcel Dekker, pp. 393 to 411 (2000).

* cited by examiner

MICROPARTICLES

TECHNICAL FIELD

The present invention lies within the field of galenic formulations for the administration of biologically active substances, more precisely microparticles for controlled release suitable for parenteral administration of biologically active substances, especially drugs. More specifically, it relates to a novel production process for such microparticles containing a biologically active substance and to novel microparticles for controlled release obtainable thereby.

BACKGROUND TO THE INVENTION

Many drugs have to be administered by injection, since they are either subjected to degradation or are insufficiently absorbed when they are given, for example, orally or nasally or by the rectal route. A drug preparation intended for parenteral use has to meet a number of requirements in order to be approved by the regulatory authorities for use on humans. It must therefore be biocompatible and biodegradable and all used substances and their degradation products must be non-toxic. In addition, particulate drugs intended for injection have to be small enough to pass through the injection needle, which preferably means that they should be smaller than 200 $\mu$m. The drug should not be degraded in the preparation to any great extent during production or storage thereof or after administration and should be released in a biologically active form with reproducible kinetics.

One class of polymers which meets the requirements of biocompatibility and biodegradation into harmless end products is the linear polyesters based on lactic acid, glycolic acid and mixtures thereof. These polymers will also hereinafter be referred to as PLGA. PLGA is degraded by ester hydrolysis into lactic acid and glycolic acid and has been shown to possess excellent biocompatibility. The innocuous nature of PLGA can be exemplified, moreover, by the approval by the regulating authorities, including the US Food and Drug Administration, of several parenteral delayed release preparations based on these polymers.

Parenterally administrable delayed release products currently on the market and based on PLGA include Decapeptyl™ (Ibsen Biotech), Prostap SR™ (Lederle), Decapeptyl® Depot (Perring) and Zoladex® (Zeneca). The drugs in these preparations are all peptides. In other words, they consist of amino acids condensed into a polymer having a relatively low degree of polymerization and they do not have any well-defined three-dimensional structure. This, in turn, usually allows the use of relatively stringent conditions during the production of these products. For example, extrusion and subsequent size-reduction can be utilized, which techniques would probably not be allowed in connection with proteins, since these do not, generally speaking, withstand such stringent conditions.

Consequently, there is also a need for controlled release preparations for proteins. Proteins are similar to peptides in that they also consist of amino acids, but the molecules are larger and the majority of proteins are dependent on a well-defined three-dimensional structure as regards many of their properties, including biological activity and immunogenicity. Their three-dimensional structure can be destroyed relatively easily, for example by high temperatures, surface-induced denaturation and, in many cases, exposure to organic solvents. A very serious drawback connected with the use of PLGA, which is an excellent material per se, for delayed release of proteins is therefore the need to use organic solvents to dissolve the said PLGA, with the attendant risk that the stability of the protein will be compromised and that conformation changes in the protein will lead to an immunological reaction in the patient, which can produce both a loss of therapeutic effect, through the formation of inhibitory antibodies, and toxic side effects. Since it is extremely difficult to determine with certainty whether a complex protein has retained its three-dimensional structure in every respect, it is very important to avoid exposing the protein to conditions which might induce conformation changes.

Despite intense efforts aimed at modifying the PLGA technology in order to avoid this inherent problem of protein instability during the production process, progress within this field has been very slow, the main reason probably being that the three-dimensional structures for the majority of proteins are far too sensitive to withstand the manufacturing conditions used and the chemically acidic environment formed with the degradation of PLGA matrices. The scientific literature contains a large number of descriptions of stability problems in the manufacture of microspheres of PLGA owing to exposure to organic solvents. As an example of the acidic environment which is formed upon the degradation of PLGA matrices, it has recently been shown that the pH value in a PLGA microsphere having a diameter of about 40 $\mu$m falls to 1.5, which is fully sufficient to denature, or otherwise damage, many therapeutically usable proteins (Fu et al, Visual Evidence of Acidic Environment Within Degrading Poly(lactic-co-glycolic acid) (PLGA) Microspheres, Pharmaceutical Research, Vol. 17, No. 1, 2000, 100–106). Should the microspheres have a greater diameter, the pH value can be expected to fall further owing to the fact that the acidic degradation products then get more difficult to diffuse away and the autocatalytic reaction is intensified. The nature of PLGA biodegradation is such that the degradation products formed are able to catalyze further hydrolysis, by virtue of their acid groups, and this leads to an intensive biodegradation and high rate of biodegradation, and consequently a substantial reduction of the pH inside the microparticles, some weeks, or months, after injection of the formulation.

The technique which is currently most commonly used to encapsulate water-soluble substances, such as proteins and peptides, is the use of multiple emulsion systems. The drug substance is dissolved in an aqueous or buffer solution and subsequently mixed with an organic solvent, immiscible with water, containing the dissolved polymer. An emulsion is formed which has the aqueous phase as the inner phase. Different types of emulsifiers and vigorous mixing are often used to create this first emulsion. This emulsion is then transferred, under agitation, to another liquid, usually water, containing another polymer, for example polyvinyl alcohol, which produces a water/oil/water triple emulsion. The microspheres are next hardened in some way. The most common way is to utilize an organic solvent having a low boiling point, typically dichloromethane, and to distil off the solvent. If the organic solvent is not fully immiscible with water, a continuous extraction procedure can be used by adding more water to the triple emulsion. A number of variations of this general procedure are also described in the literature. In certain cases, the primary emulsion is mixed with a non-aqueous phase, for example silicone oil. Solid drug materials can also be used instead of dissolved ones.

PLGA microspheres containing proteins are described in WO-A1-9013780, in which the main feature is the use of very low temperatures during the production of the microspheres for the purpose of preserving high biological activity in the proteins. The activity for encapsulated superoxide dismutase is measured, but only on the part which has been released from the particles. This method has been used to produce PLGA microspheres containing human growth hormone in WO-A1-9412158, wherein human growth hormone is dispersed in methylene chloride containing PLGA, the obtained dispersion is sprayed into a container of frozen ethanol beneath a layer of liquid nitrogen in order to freeze the fine droplets and said droplets are allowed to settle in the nitrogen on the ethanol. The ethanol is subsequently thawed and the microspheres start to sink in the ethanol, where the methylene chloride is extracted in the ethanol and the microspheres are hardened. Using this methodology, the protein stability can be better retained than in the majority of other processes for enclosing proteins in PLGA microspheres, and a product has also recently been approved by the regulatory authorities in the USA. However, this still remains to be clearly demonstrated for other proteins and the problem remains of exposing the enclosed biologically active substance to a very low pH during the degradation of the PLGA matrix.

In the aforementioned methods based on encapsulation with PLGA, the active substances are still exposed to an organic solvent and this, generally speaking, is harmful to the stability of a protein. Moreover, the discussed emulsion processes are complicated and probably problematical in any attempt to scale up to an industrial scale. Furthermore, many of the organic solvents which are utilized in many of these processes are associated with environmental problems and their high affinity for the PLGA polymer makes their removal difficult.

A number of attempts to solve the above-described problems caused by exposure of the biologically active substance to a chemically acidic environment during the biodegradation of the microsphere matrix and organic solvents in the manufacturing process have been described. In order to avoid an acidic environment during the degradation, attempts have been made to replace PLGA as the matrix for the microspheres by a polymer which produces chemically neutral degradation products, and in order to avoid exposing the biologically active substance to organic solvents, either it has been attempted to manufacture the microspheres in advance and, only once they have been processed and dried, to load them with the biologically active substance, or attempts have been made to exclude or limit the organic solvent during manufacture of the microspheres.

By, way of example, highly branched starch of relatively low molecular weight (maltodextrin, average molecular weight about 5000 Da) has been covalently modified with acryl groups for conversion of this starch into a form which can be solidified into microspheres and the obtained polyacryl starch has been converted into particulate form by radical polymerization in an emulsion with toluene/chloroform (4:1) as the outer phase (Characterization of Polyacryl Starch Microparticles as Carriers for Proteins and Drugs, Arturason et al, J Pharm Sci, 73, 1507–1513, 1984). Proteins were able to be entrapped in these microspheres, but the manufacturing conditions expose the biologically active substance to both organic solvents and high shearing forces in the manufacture of the emulsion. The obtained microspheres are dissolved enzymatically and the pH can be expected to be kept neutral. The obtained microspheres are not suitable for parenteral administrations, especially repeated parenteral administration, for a number of reasons. Most important of all is the incomplete and very slow biodegradability of both the starch matrix (Biodegradable Microspheres IV. Factors Affecting the Distribution and Degradation of Polyacryl Starch Microparticles, Laakso et al, J Pharm Sci 75, 962–967, 1986) and the synthetic polymer chain which cross-links the starch molecules. Moreover, these microspheres are far too small, <2 μm in diameter, to be suitable for injection in the tissues for sustained release, since tissue macrophages can easily phagocytize them. Attempts to raise the degradation rate and the degree of degradation by introducing a potentially biodegradable ester group in order to bond the acryl groups to the highly branched starch failed to produce the intended result and even these polyacryl starch microspheres were biodegraded far too slowly and incompletely over reasonable periods of time (BIODEGRADABLE MICROSPHERES: Some Properties of Polyacryl Starch Microparticles Prepared from Acrylic acid Esterified Starch, Laakso and Sjöholm, 1987 (76), pp. 935–939, J Pharm Sci.)

Microspheres of polyacryl dextran have been manufactured in two-phase aqueous systems (Stenekes et al, The Preparation of Dextran Microspheres in an All-Aqueous System: Effect of the Formulation Parameters on Particle Characteristics, Pharmaceutical Research, Vol. 15, No. 4, 1998, 557–561, and Franssen and Hennink, A novel preparation method for polymeric microparticles without using organic solvents, Int J Pharm 168, 1–7, 1998). With this mode of procedure, the biologically active substance is prevented from being exposed to organic solvents but, for the rest, the microspheres acquire properties equivalent to the properties described for the polyacryl starch microspheres above, which makes them unsuitable for repeated parenteral administrations. Bearing in mind that man does not have specific dextran-degrading enzymes, the degradation rate should be even lower than for polyacryl starch microspheres. The use of dextran is also associated with a certain risk of serious allergic reactions.

Manufacture of starch microspheres with the use of non-chemically-modified starch using an oil as the outer phase has been described (U.S. Pat. No. 4,713,249; Schröder, U., Crystallized carbohydrate spheres for slow release and targeting, Methods Enzymol, 1985 (112), 116–128; Schröder, U., Crystallized carbohydrate spheres as a slow release matrix for biologically active substances, Bio-materials 5:100–104, 1984). The microspheres are solidified in these cases by precipitation in acetone, which leads both to the exposure of the biologically active substance to an organic solvent and to the non-utilization, during the manufacturing process, of the natural tendency of the starch to solidify through physical cross-linking. This leads, in turn, to microspheres having inherent instability, since the starch, after resuspension in water and upon exposure to body fluids, will endeavour to form such cross-links. In order for a water-in-oil emulsion to be obtained, high shear forces are required and the microspheres which are formed are far too small to be suitable for parenteral sustained release.

EP 213303 A2 describes the production of microspheres of, inter alia, chemically unmodified starch in two-phase aqueous systems, utilizing the natural capacity of the starch to solidify through the formation of physical cross-links, and the immobilization of a substance in these microspheres for the purpose of avoiding exposure of the biologically active substance to organic solvents. The described methodology, in combination with the starch quality which is defined, does not give rise to fully biodegradable particles. Neither are the obtained particles suitable for injection, particularly for repeated injections over a longer period, since the described starch quality contains far too high quantities of foreign vegetable protein. In contrast to what is taught by this patent, it has now also surprisingly been found that significantly better yield and higher loading of the biologically active molecule can be obtained if significantly higher concentrations of the polymers are used than is required to form the two-phase aqueous system and that this also leads to advantages in terms of the conditions for obtaining stable, non-aggregated microspheres and their size distribution. The temperature treatments which are described cannot be used for sensitive macromolecules and the same applies to the processing which comprises drying with either ethanol or acetone.

Alternative methods for the manufacture of microspheres in two-phase aqueous systems have been described. In U.S. Pat. No. 5,981,719, microparticles are made by mixing the biologically active macromolecule with a polymer at a pH close to the isoelectric point of the macromolecule and stabilizing the microspheres through the supply of energy, preferably heat. The lowest share of macromolecule, i.e the biologically active substance, in the preparation is 40%, which for most applications is too high and leads to great uncertainty in the injected quantity of active substance, since the dose of microparticles becomes far too low. Even though the manufacturing method is described as mild and capable of retaining the biological activity of the entrapped biologically active substance, the microparticles are stabilized by heating and, in the examples given, heating is effected to at least 58° C. for 30 min. and, in many cases, to 70–90° C. for an equivalent period, which cannot be expected to be tolerated by sensitive proteins, the biological activity of which is dependent on a three-dimensional structure, and even where the protein has apparently withstood the manufacturing process, there is still a risk of small, but nonetheless not insignificant changes in the conformation of the protein. As the outer phase, a combination of two polymers is always used, generally polyvinyl pyrrolidone and PEG, which complicates the manufacturing process in that both these substances must be washed away from the microspheres in a reproducible and reliable manner. The formed microparticles are too small (in the examples, values below 0.1 μm in diameter are quoted) to be suitable for parenteral sustained release after, for example, subcutaneous injection, since macrophages, which are cells which specialize in phagocytizing particles and which are present in the tissues, are easily capable of phagocytizing microspheres up to 5–10, possibly 20 μm, and the phagocytized particles are localized intracellularly in the lysosomes, where both the particles and the biologically active substance are degraded, whereupon the therapeutic effect is lost. The very small particle size also makes the processing of the microspheres more complicated, since desirable methods, such as filtration, cannot be used. The equivalent applies to U.S. Pat. No. 5,849,884, U.S. Pat. No. 5,578,709 and EP 0 688 429 B1 describe the use of two-phase aqueous systems for the manufacture of macromolecular microparticle solutions and chemical or thermal cross-linking of the dehydrated macromolecules to form microparticles. It is entirely undesirable to chemically cross-link the biologically active macromolecule, either with itself or with the microparticle matrix, since chemical modifications of this kind have a number of serious drawbacks, such as reduction of the bioactivity of a sensitive protein and risk of induction of an immune response to the new antigenic determinants of the protein, giving rise to the need for extensive toxicological studies to investigate the safety of the product. Microparticles which are made through chemical cross-linking with glutaraldehyde are previously known and are considered generally unsuitable for repeated administrations parenterally to humans. The microparticles which are described in U.S. Pat. No. 5,578,709 suffer in general terms from the same drawbacks as are described for U.S. Pat. No. 5,981,719, with unsuitable manufacturing conditions for sensitive proteins, either through their exposure to chemical modification or to harmful temperatures, and a microparticle size distribution which is too narrow for parenteral, sustained release and which complicates post-manufacture processing of the microspheres.

WO 97/14408 describes the use of air-suspension technology for producing microparticles for sustained release after parenteral administration, without the biologically active substance being exposed to organic solvents. However, the publication provides no guidance towards the process according to the invention or towards the novel microparticles which can thereby be obtained.

In U.S. Pat. No. 5,470,582, a microsphere consisting of PLGA and containing a macromolecule is produced by a two-stage process, in which the microsphere as such is first manufactured using organic solvents and then loaded with the macromolecule at a later stage in which the organic solvent has already been removed. This procedure leads to far too low a content of the biologically active substance, generally 1–2%, and to a very large fraction being released immediately after injection, which very often is entirely unsuitable. This far too rapid initial release is already very high given a 1% load and becomes even more pronounced when the active substance content in the microspheres is higher. Upon the degradation of the PLGA matrix, the pH falls to levels which are generally not acceptable for sensitive macromolecules.

Attempts to improve the stability of proteins encapsulated in PLGA or PLA matrices have been described in great detail in US 2002 0009493 A1, By incorporation of basic salts the microclimate of the PLGA devices or microspheres has been neutralized. However, this neutralization is not homogenous and additional excipients are necessary to improve the pH control. When the content of the biologically active substance is low, for instance, a carrier is needed for sufficient formation of an interconnected network of pores; or, a pore-forming agent or a low concentration of the PLA or PLGA polymer, or other excipients such as sucrose to increase release duration, or the use of low molecular weight PLGA copolymer with co-encapsulation of basic salts, or the use of a new oil-in-oil emulsion system. For example, it is necessary to have a 15% protein loading of BSA to enable the base to diffuse to the BSA-containing pores. It is highly undesirable that the loading of the biologically active substance has to be determined by such considerations. Even when an oil-in-oil (O/O) emulsion system was used instead of the more established W/O/W emulsion system, a high burst, which increased with loading, and a dependence on the LA/GA ration of PLGA on the stability of the encapsulated BSA during release remained.

When a biologically active substance, rhBMP-2 was to be formulated it was attempted first to increase its stability by adding heparin and co-encapsulate BSA, which had to be abandoned due to significant bleeding surrounding the implants, second by decreasing the pH of the buffer, which necessitated removal of BSA as an excipient due to its low stability at low pH, and co-encapsulation with a base. Even the microsphere formulation having the highest stability of rhBMP-2 had about 35% remaining in the microspheres after 28 days of release. For tPA complete release in vitro was obtained with co-encapsulation of magnesium hydroxide. When another biologically active substance, bFGF, was to be encapsulated five additives were used: magnesium hydroxide, BSA, heparin, EDTA and sucrose.

Despite describing a vast array of approaches to increase the neutralization of the acidic microclimate found in PLGA based devices, including microspheres, US 2002 0009493 does not provide a general solution to the problem but rather indirectly highlights the complexity and limitations related to the use of PLGA or PLA polymers as a matrix for the delivery of sensitive biologically active proteins. In addition, no method avoiding exposing the protein to an organic solvent during manufacture is provided. No method allowing encapsulation of the biologically active substance in a polymer, which upon degradation yields chemically neutral degradation products, therefore being inherently more capable of providing homogeneously a less acidic microenvironment in the close proximity of the biologically active substance, is provided. No method to avoid generation and accumulation of acidic degradation products in the interior, or center, of the device or microsphere is provided. No method where the excipients to be used to improve the stability of the biologically active substance during encapsulation or release can be selected independently of any excipients used to control the release of the biologically active substance is provided.

That starch is, in theory, a very suitable, perhaps even ideal, matrix material for microparticles has been known for a long time, since starch does not need to be dissolved in organic solvents and has a natural tendency to solidify and since there are enzymes within the body which can break down the starch into endogenic and neutral substances, ultimately glucose, and since starch, presumably owing to the similarity with endogenic glycogen, has been shown to be non-immunogenic. Despite intense efforts, starch having properties which enable manufacture of microparticles suitable for parenteral use and conditions which enable manufacture of fully biodegradable microparticles under mild conditions, which allow sensitive, biologically active substances, such as proteins, to become entrapped, has not been previously described.

Starch granules naturally contain impurities, such as starch proteins, which makes them unsuitable for injection parenterally. In the event of unintentional depositing of insufficiently purified starch, such as can occur in operations where many types of operating gloves are powdered with stabilized starch granules, very serious secondary effects can arise. Neither are starch granules intrinsically suitable for repeated parenteral administrations, for the reason that they are not fully biodegradable within acceptable time spans.

Starch microspheres made of acid-hydrolyzed and purified starch have been used for parenteral administration to humans. The microspheres were made by chemical cross-linking with epichlorohydrin under strongly alkaline conditions. The chemical modification which was then acquired by the starch leads to reduced biodegradability, so that the microspheres can be fully dissolved by endogenic enzymes, such as α-amylase, but not converted fully into glucose as the end product. Neither the manufacturing method nor the obtained microspheres are suitable for the immobilization of sensitive proteins, nor is such acid-hydrolyzed starch, which is essentially based on hydrolyzed amylose, suitable for producing either fully biodegradable starch microspheres or starch microspheres containing a high load of a biologically active substance, such as a protein.

Hydroxyethyl starch (HES) is administered parenterally to humans in high doses as a plasma substitute, HES is produced by starch granules from starch consisting broadly exclusively of highly branched amylopectin, so-called "waxy maize", being acid-hydrolyzed in order to reduce the molecular weight distribution and being subsequently hydroxyethylated under alkaline conditions and acid-hydrolyzed once more to achieve an average molecular weight of around 200,000 Da. After this, filtration, extraction with acetone and spray-drying are carried out. The purpose of the hydroxyethylation is to prolong the duration of the effect, since non-modified amylopectin is very rapidly degraded by α-amylase and its residence time in the circulation is ca. 10 minutes. HES is not suitable for the production of fully biodegradable microspheres containing a biologically active substance, since the chemical modification leads to a considerable fall in the speed and completeness of the biodegradation and results in the elimination of the natural tendency of the starch to solidify through the formation of non-covalent cross-linkings. Moreover, highly concentrated solutions of HES become far too viscous to be usable for the production of microparticles. The use of HES in these high doses shows that parenterally usable starch can be manufactured, even though HES is not usable for the manufacture of microspheres without chemical cross-linking or precipitation with organic solvents.

WO 99/00425 describes the use of heat-resistant proteolytic enzymes with wide pH-optimum to purge starch granules of surface-associated proteins. The obtained granules are not suitable for parenteral administration, since they still contain the starch proteins which are present within the granules and there is a risk that residues of the added proteolytic enzymes will be left in the granules. Neither are the granules suitable for the manufacture of parenterally administrable starch microspheres in two-phase aqueous systems, since they have the wrong molecular weight distribution to be able to be used in high enough concentration, even after being dissolved, and, where microspheres can be obtained, they are probably not fully biodegradable.

The use of shearing to modify the molecular weight distribution of starch, for the purpose of producing better starch for the production of tablets, is described in U.S. Pat. No. 5,455,342 and WO 93/21008. The starch which is obtained is not suitable for parenteral administration owing to the high content of starch proteins, which might be present in denatured form after the shearing, and neither is the obtained starch suitable for producing biodegradable starch microspheres for parenteral administration or for use in two-phase aqueous systems for the production of such starch microspheres. Shearing has also been used to manufacture hydroxyethyl starch, as is disclosed in WO 96/10042. However, for similar reasons such hydroxyethyl starch is not either suitable for parenteral administration or for the production of microspheres as referred to above.

A process for the production of parenterally administrable microparticle preparations having the following features would therefore be extremely desirable:

a process which makes it possible to entrap sensitive, biologically active substances in microparticles with retention of their biological activity;

a process by means of which biologically active substances can be entrapped under conditions which do not expose them to organic solvents, high temperatures or high shear forces and which allows them to retain their biological activity;

a process which permits high loading of a parenterally administrable preparation with even sensitive, biologically active substances;

a process by means of which a substantially fully biodegradable and biocompatible preparation can be produced, which is suitable for injecting parenterally and upon whose degradation chemically neutral endogenic substances are formed;

a process by means of which a parenterally injectable preparation having a size exceeding 20 μm and, preferably exceeding 30 μm, is produced for the purpose of avoiding phagocytosis of tissue macrophages and which simplifies processing of the same during manufacture;

a process for the production of microparticles containing a biologically active substance, which microparticles can be used as intermediate product in the production of a preparation for controlled, sustained or delayed release and which permit rigorous quality control of the chemical stability and biological activity of the entrapped biological substance;

a process which utilizes a parenterally acceptable starch which is suitable for the production of substantially fully biodegradable starch microparticles;

a substantially fully biodegradable and biocompatible microparticulate preparation which is suitable for injecting parenterally and upon whose degradation chemically neutral endogenic substances are formed;

a microparticle preparation containing a biologically active substance and having a particle size distribution which is suitable for coating by means of air suspension technology and having sufficient mechanical strength for this purpose;

a microparticle preparation containing sufficient buffering capacity to enable a maintenance of the pH of the microparticle interior at a sufficiently high level to retain the bioactivity of the encapsulated biologically active substance.

Objects such as these and other objects are achieved by means of the invention defined below.

DESCRIPTION OF THE INVENTION

Figure 1:
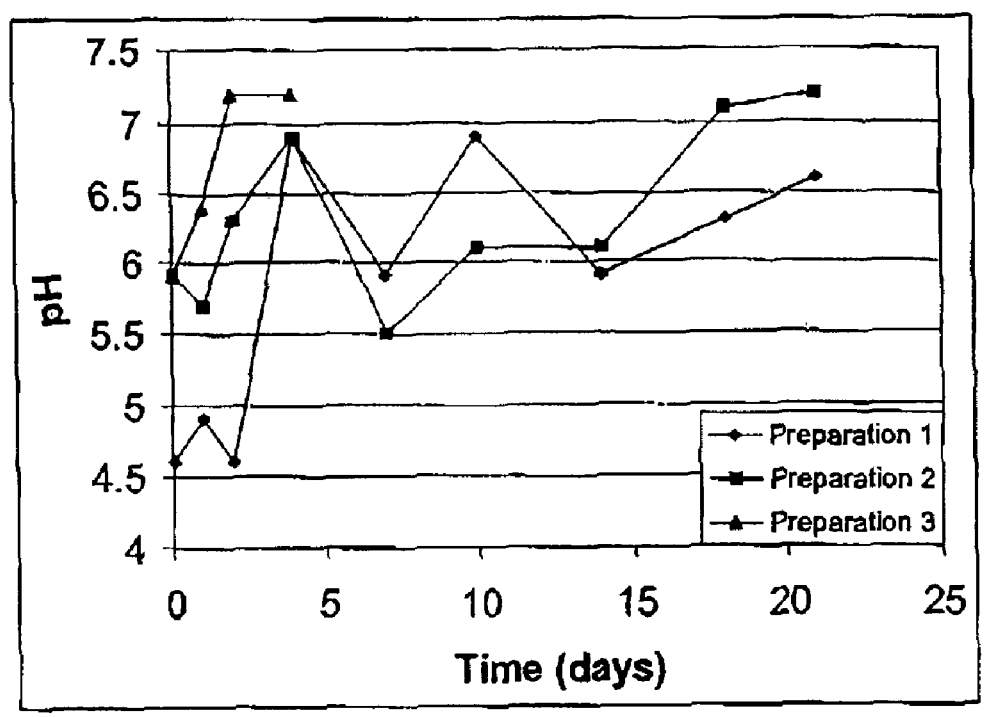
FIG 1. Determination of the pH inside microspheres. The results show pH versus time during in vitro release as indicated.

According to a first aspect of present invention, it relates to a process for production of microparticles. More specifically it relates to production of microparticles which contain a biologically active substance, especially a substance that is sensitive to an acidic pH. Primarily said microparticles are intended for parenteral administration of the said substance to a mammal, especially a human. The said parenteral administration primarily means that the microparticles are intended for injection.

Since the microparticles are primarily intended for injection, it is a question especially of manufacturing particles with an average diameter within the range of 10–200 μm, generally 20–100 μm and in particular 20–80 μm.

The expression "microparticles" is used in connection with the invention as a general designation for particles of a certain size known in the art. One type of microparticles is that of microspheres which have in the main a spherical shape, although the term microparticle may generally include deviations from such an ideal spherical shape. The term microcapsule known in the art is also covered by the expression microparticle in accordance with the known art.

An object of the invention is to accomplish microparticles which create a good microclimate for the biologically active substance incorporated therein such that the bioactivity of said substance is essentially maintained during the manufacturing process as well as after administration. This for instance means that the microparticles are especially suitable for substances which are sensitive to acidic pH-values, organic solvents and/or high temperatures, for instance recombinant proteins.

Especially non-acidic environments are created and maintained for the biologically active substances.

According to one aspect of the invention this is achieved by a process which comprises:

a) preparing of an aqueous starch solution containing starch, which has an amylopectin content in excess of 85 percent by weight, in which the molecular weight of said amylopectin has been reduced such that at least 80 percent by weight of the material lies within the range of 10–10000 kDa, and which has an amino acid nitrogen content of less than 50 μg per g dry weight of starch, b) combining the biologically active substance with the starch solution under conditions such that a composition is formed in the form of a solution, emulsion or suspension of said substance in the starch solution, c) mixing the composition obtained in step b) with an aqueous solution of a polymer having the ability to form a two-phase aqueous system, so that an emulsion of starch droplets is formed which contain the biologically active substance as an inner phase in an outer phase of said polymer solution, d) causing or allowing the starch droplets obtained in step c) to gel into starch particles through the natural propensity of the starch to solidify, e) drying the starch particles, and f) optionally applying a release-controlling shell of a biocompatible and biodegradable polymer, preferably by an air suspension method, to the dried starch particles, wherein at least one buffer substance having the ability of keeping the pH of the produced microparticles above 3 if exposing the microparticles to an aqueous environment, e.g. by injection into a mammal, including man, is added at any stage during the process.

The process is thus based on the use of a certain type of starch as microparticle matrix. One starch that is especially suitable, and a process for the production thereof, are described in the Swedish patent application No. 0003616-0. In this case the molecular weight reduction is accomplished by shearing. Another useful starch is disclosed in PCT application No. SE 01/02168. In last-mentioned case the molecular weight reduction is accomplished by acid hydrolysis.

Details about the starch may in other words be obtained from said patent applications, the contents of which are thus in this respect introduced into the present text by way of reference.

Some further important features of such a starch will, however, be described below. In order that fully biodegradable microparticles with high active substance yield shall be formed in a two-phase aqueous system and in order that the obtained starch microparticles shall have the properties to be described below, the starch must generally predominantly consist of highly branched starch, which, in the natural state in the starch granule, is referred to as amylopectin. It should also have a molecular weight distribution which makes it possible to achieve desired concentrations and gelation rates.

It may be added, in this context, that the term "biodegradable" means that the microparticles, after parenteral administration, are dissolved in the body to form endogenic substances, ultimately, for example, glucose, The biodegradability can be determined or examined through incubation with a suitable enzyme, for example alpha-amylase, in vitro.

It is in this case appropriate to add the enzyme a number of times during the incubation period, so as thereby to ensure that there is active enzyme permanently present in the incubation mixture. The biodegradability can also be examined through parenteral injection of the microparticles, for example subcutaneously or intramuscularly, and histological examination of the tissue as a function of time.

Biodegradable starch microparticles disappear normally from the tissue within a few weeks and generally within one week. In those cases in which the starch microparticles are coated with a release-controlling shell, for example coated, it is generally this shell which determines the biodegradability rate, which then, in turn, determines when alpha-amylase becomes available to the starch matrix.

The biocompatibility can also be examined through parenteral administration of the microparticles, for example subcutaneously or intramuscularly, and histological evaluation of the tissue, it being important to bear in mind that the biologically active substance, which often is a protein, has in itself the capacity to induce, for example, an immunodefence if administered in another species. For example, a large number of recombinantly produced human proteins can give rise to an immune response in test animals.

The starch must further have a purity which is acceptable for the manufacture of a parenterally administrable preparation. It must also be able to form sufficiently stable solutions in sufficiently high concentration to enable the biologically active substance to be mixed in under conditions allowing the retention of the bioactivity of the substance, at the same time as it must spontaneously be able to be solidified in a controlled manner in order to achieve stable, yet at the same time biodegradable, microparticles. High concentration of the starch is also important to prevent the biologically active substance from being distributed out to an unacceptable extent to the outer phase or to the interface between the inner and the outer phases.

A number of preferred embodiments with regard to the character of the starch are as follows.

The starch preferably has a purity of at most 20 µg, more preferably at most 10 µg, and most preferably at most 5 µg, amino acid nitrogen per g dry weight of starch.

The molecular weight of the above mentioned amylopectin is preferably reduced, such that at least 80% by weight of the material lies within the range of 100–4000 kDa, more preferably 200–1000 kDa, and most preferably 300–600 kDa.

In addition, the starch preferably has an amylopectin content with the reduced molecular weight in question exceeding 95% by weight, more preferably exceeding 98% by weight. It can also, of course, consist of 100% by weight of such amylopectin.

According to another preferred embodiment, the starch is of such a type that it can be dissolved in water in a concentration exceeding 25% by weight. This means, in general, a capacity to dissolve in water according to a technique which is known per se, i.e. usually dissolution at elevated temperature, for example up to approximately 80° C.

According to a further preferred embodiment, the starch is substantially lacking in covalently bonded extra chemical groups of the type which are found in hydroxyethyl starch. By this is meant, in general, that the starch essentially only contains groups of the type which are found in natural starch and have not been in any way modified, such as in hydroxyethyl starch, for example.

Another preferred embodiment involves the starch having an endotoxin content of less than 25 EU/g.

A further preferred embodiment involves the starch containing less than 100 microorganisms per gram, often even less than 10 microorganisms per gram.

The starch can further be defined as being substantially purified from surface-localized proteins, lipids and endotoxins by means of washing with aqueous alkali solution, reduced in molecular weight by means of shearing or acid hydrolysis, and purified from internal proteins by means of ion exchange chromatography, preferably anion exchange chromatography.

As far as the purity in all these contexts is concerned, it is in general the case that expressions of the type "essentially" or "substantially" generally mean to a minimum of 90%, for example 95%, 99% or 99.9%.

That amylopectin constitutes the main component part in the starch used means in general terms that its share is 60–100% by weight, calculated on the basis of dry weight of starch.

In certain cases, it can here be favourable to use a lesser share, for example 2–15% by weight, of short-chain amylose to modify the gelation rate in step d). The average molecular weight of the said amylose lies preferably within the range of 2.5–70 kDa, especially 5–45 kDa. Other details regarding short-chain amylose can be obtained from U.S. Pat. No. 3,881,991.

In the formation of the starch solution in step a), heating according to a technique which is known per se is in general used to dissolve the starch. An especially preferred embodiment simultaneously involves the starch being dissolved under autoclaving, it also preferably being sterilized. This autoclaving is realized in aqueous solutions, for example water for injection or suitable buffer.

If the biologically active substance is a sensitive protein or another temperature-sensitive substance, the starch solution must cool to an appropriate temperature before being combined with the substance in question. What temperature is appropriate is determined firstly by the thermal stability of the biologically active substance, but in purely general terms a temperature of less than ca. 60° C., preferably less than 55° C., is appropriate.

According to a preferred embodiment, the active substance is therefore combined with the starch solution at a temperature of at most 60° C., more preferably at most 55° C., and most preferably within the range of 20–45° C., especially 30–37° C.

For the mixing operation in step b), furthermore, a weight ratio of starch:biologically active substance within the range of 3:1 to 10000:1, preferably 3:1 to 100:1, is expediently used.

It is also the case for the mixing operation that the active substance is mixed with the starch solution before a two-phase aqueous system is formed in step c). The active substance can be in dissolved form, for example in a buffer solution, or in solid, amorphous or crystalline form, and at a suitable temperature, which is generally between room temperature (20° C.) and 45° C., preferably at most 37° C. It is possible to add the starch solution to the biologically active substance, or vice versa. Since the biologically active substances suitable for use in this system, for example proteins, are generally macromolecules, it is possible, when mixing a solution of a dissolved macromolecule with starch, for an emulsion to form, in which the macromolecule generally represents the inner phase, or a precipitate. This is entirely acceptable, provided that the biologically active substance retains or does not appreciably lose its bioactivity. A homogeneous solution, emulsion or suspension is then created by agitation, which can be carried out using a suitable technique. Such a technique is well known within the field, examples which might be quoted being magnetic agitation, propeller agitation or the use of one or more static mixers. An especially preferred embodiment of the invention is represented in this case by the use of propeller agitation.

In the production of the starch microparticles according to the present invention, the concentration of starch in the solution which is to be converted to solid form and in which the biologically active substance is to be incorporated should preferably be at least 20% by weight to enable the formation of starch microparticles having good properties. Exactly what starch concentration works best in each individual case can be titrated out in a simple manner for each individual biologically active substance, where the load in the microparticles is that which is required in the individual case. In this context, it should be noted that the biologically active substance, and other substances, to be incorporated in the microparticles can affect the two-phase system and the gelation properties of the starch, which also means that customary preparatory trials are conducted for the purpose of determining the optimal conditions in the individual case. Trials generally show that the starch concentration should advantageously be at least 30% by weight and in certain specific cases at least 40% by weight. As the highest limit, 50% by weight is usually applicable, especially at most 45% by weight. It is not normally possible to obtain these high starch concentrations without the use of molecular-weight-reduced, highly branched starch.

Regarding the polymer used in step c) for the purpose of forming a two-phase aqueous system, information is published, within precisely this technical field, on a large number of polymers with the capacity to form two-phase systems with starch as the inner phase. All such polymers must be considered to lie within the scope of the present invention. An especially suitable polymer in this context, however, is polyethylene glycol. This polyethylene glycol preferably has an average molecular weight of 5–35 kDa, more preferably 15–25 kDa and especially about 20 kDa.

The polymer is dissolved in suitable concentration in water or aqueous solution, which expression also includes buffer solution, and is temperature-adjusted to a suitable temperature. This temperature lies preferably within the range of 4–50° C., more preferably 10–40° C. and most preferably 10–37° C. The concentration of the polymer in the aqueous solution is at least 20% by weight and preferably at least 30% by weight, and more expediently at most 45% by weight. An especially preferred range is 30–40% by weight.

The mixing operation in step c) can be executed in many different ways, for example through the use of propeller agitation or at least one static mixer. The mixing is normally carried out within the temperature range of 4–50° C., preferably 20–40° C., often about 37° C. In a batch process, the starch solution can be added to the polymer solution or vice versa. Where static mixers or blenders are utilized, the operation is expediently executed by the two solutions being pumped in two separate pipelines into a common pipeline containing the blenders.

The emulsion can be formed using low shearing forces, since there is no high surface tension present between the phases in water/water emulsions, in contrast to oil/water or water/oil emulsions, and in this case it is primarily the viscosity of the starch solution which has to be overcome for the droplets to achieve a certain size distribution. In most cases, magnetic or propeller agitation is sufficient. On a larger scale, for example when the quantity of microparticles to be produced exceeds 50 g, it is expedient to use so-called baffles to obtain even more effective agitation in the container which is used. An alternative way of forming the water/water emulsion is to use at least one static mixer, the starch solution expediently being pumped at regulated speed in a pipe in which the static mixers have been placed. The pumping can be effected with any type of suitable pump, provided that it gives an even flow rate under these conditions, does not expose the mixture to unnecessarily high shear forces and is acceptable for the manufacture of parenteral preparations in terms of purity and non-leakage of unwanted substances. In those cases, too, in which static mixers are used to create the emulsion, it is generally advantageous to have the solidification into microparticles take place in a vessel with suitable agitation.

A preferred embodiment of the process according to the invention means that in step c) the polymer solution is added to the composition in at least two stages, in which an admixture is effected after the emulsion has been created or has begun to be created.

It is also within the scope of the present invention, of course, to add the polymer solutions in many stages and to change, for example, the average molecular weight and/or concentration of the polymer used, for example in order to increase the starch concentration in the inner phase where this is desirable.

The mixing operation in step c) is also expediently executed under such conditions that the starch droplets formed have the size required for the microparticles, i.e. preferably a mean diameter, in the dry state, within the range of 10–200 $\mu$m, preferably 20–100 $\mu$m, more preferably 20–80 $\mu$m.

In the production of the microparticles according to the present invention it is essential that the solidification occurs through the natural tendency or capacity of the starch to gel and not, for example, through precipitation with organic solvents, such as acetone. The latter procedure may lead to the biologically active substance being exposed to organic solvent, which in many cases is unacceptable, and to an absence of the natural formation of the physical cross-linkages that are required in order to obtain stable microparticles in a controlled manner.

In connection with the solidification of the microparticles, it is important that this should take place under conditions which are mild for the incorporated biologically active substance(s). In other words, it is primarily a question of using a temperature which is not harmful to the current substance. In this context, it has surprisingly been shown that the criteria for this and for the formation of stable microparticles with suitable size distribution can more easily be met if, during the solidification, more than one temperature or temperature level is used. It is especially advantageous if the solidification process in the two-phase system is initiated at a lower temperature than the temperature which is used in the end phase of the solidification. A preferred embodiment means that the solidification is initiated within the range of 1–20° C., preferably 1–10° C., especially around 4° C., and is concluded within the range of 20–55° C., preferably 25–40° C., especially around 37° C. In some cases, however, the active substance may be extremely sensitive to high temperatures, and in such cases the second or final stage of the solidification is preferably performed at a temperature not exceeding about 22° C. Such cases can easily be determined by the skilled artisan via pretrials and assessments of the stability of the encapsulated biologically active substance.

Confirmation that the chosen conditions are correct or appropriate can be obtained by establishing that the starch microparticles have a desired size distribution, are stable during the subsequent washing and drying operations and are dissolved substantially by fully enzymatic means in vitro and/or that the incorporated substance has been encapsulated effectively and has retained bioactivity. The last-mentioned is usually examined using chromatographic methods or using other methods established within the art, in vitro or in vivo, after the microparticles have been enzymatically dissolved under mild conditions, and is an important element in ensuring a robust and reliable manufacturing process for sensitive, biologically active substances. It is a great advantage for the microparticles to be able to be fully dissolved under mild conditions, since this minimizes the risks of preparation-induced artifacts, which are usually found when, for example, organic solvents are required to dissolve the microparticles, which is the case, for example, when these consist of a PLGA matrix.

The formed microparticles are preferably washed in a suitable manner in order to remove the outer phase and any surplus active substance. Such washing is expediently effected by filtration, which is made possible by the good mechanical stability and suitable size distribution of the microparticles. Washing by means of centrifugation, removal of the supernatant and resuspension in the washing medium may often also be appropriate. In each washing process, one or more suitable washing media are used, which generally are buffer-containing aqueous solutions. In this connection, sieving can also be used, if required, in order to adjust the size distribution of the microparticles, for example to eliminate the content of too small microparticles and to ensure that no microparticles above a certain size are present in the finished product.

The microparticles can be dried in any way appropriate, for example by spray-drying, freeze-drying or vacuum-drying. Which drying method is chosen in the individual case often depends on what is most appropriate for the retention of the biological activity for the enclosed biologically active substance. Process considerations also enter into the picture, such as capacity and purity aspects. Freeze-drying is often the preferred drying method, since, correctly designed, it is especially mild with respect to the enclosed biologically active substance. That the incorporated biologically active substance has retained its bioactivity can be established by means of analysis appropriate to the microparticle after the microparticle has been enzymatically dissolved under mild conditions. Suitable enzymes for use in connection with starch are alpha-amylase and amyloglucosidase, singly or in combination, it being important to establish, where appropriate, that they are free from possible proteases, which can degrade proteins. The presence of proteases can be detected with methods known within the field and, for example, by mixing the biologically active substance in control trials and determining its integrity in the usual manner after incubation with the intended enzyme mixture under the conditions which will afterwards be used to dissolve the microparticles.

The enzymes used may need to be purified from contaminating proteases, for example, in order to avoid artifactual degradation of sensitive substances, such as recombinant proteins, for example, incorporated into the microparticles. This can be done using techniques known within the field, for example by chromatography with $\alpha_2$-macroglobulin bonded to a suitable chromatography material.

In order to modify the release properties for the microparticles, a release-controlling shell, or coating, made from a biocompatible and biodegradable polymer might also be applied. Examples of suitable polymers in this context are found in the prior art, for example EP 535 937, and polymers of lactic acid and glycolic acid (PLGA) can especially be mentioned. The shell in question is preferably applied using air suspension technology. An especially suitable technique of this kind is described in WO97/14408 and details in this regard can thus be obtained from this publication, the content of which is included in the text by reference. The starch microparticles which are obtained by means of the process according to the present invention are extremely well suited to coating or coating by means of the said air suspension technology, and the coated microparticles obtained are especially well suited to parenteral administration.

An important aspect of this invention is the control of the pH inside the microparticles. As has already been described a distinct disadvantage with e.g. PLGA technology is that the pH inside the microparticles often falls to levels harmful for the biologically active substance as a consequence of the biodegradation of PLG that occurs some time after injection. One significant improvement is the substitution of a fraction of the PLGA with a polymer which provides neutral degradation products, such as parenterally useful starch described in connection with the present invention, and which forms the interior of the microparticle and with the coating, consisting for example of PLGA, being located on the exterior of the microparticle and as close to the surrounding tissue as possible to provide for improved diffusion of the acid metabolites generated during biodegradation of the PLGA coating to the surrounding tissue.

This results in essentially no accumulation of acid metabolites in the interior, or center, of the microparticles during degradation of the polymer capable of causing a low pH, for example, when the polymer is a homopolymer or copolymer containing $\alpha$-hydroxy acid units.

It has however suprisingly been found that when a microparticle preparation with the above mentioned characteristics is placed in an aqueous medium, either in vitro or as a consequence of being injected into a mammal, a transient decrease in pH, which may be able to adversely affect the stability and/or release of some acid sensitive substances, occurs. Thus, the unexpected changes in pH occuring during a relatively short time period after exposure to an aqueous environment, and well before any significant biodegradation of the PLGA takes place, is sufficient to adversely affect the stability and/or release of some pH-sensitive biologically active substance and thus eliminate, or reduce, the benefits to be obtained from the release of that active substance.

In connection with this, it should be emphasized that the uses of buffering substances in the prior art are not able to overcome this problem as they are chosen to provide a long lasting control of pH, but as a consequence thereof they are not able to respond sufficiently quickly and/or to a sufficient degree, to buffer the pH change occuring for example immediately after exposure of the microparticle preparation to an aqueous environment to provide a homogeneous acid neutralization (Schwendeman S P, Shenderova A. Zhu G. Jiang W. Stability of encapsulated substances in Poly (lactideco-Glycolide) delivery systems. In: Wise DL, editor. Handbook of pharmaceutical controlled release technology. New York; Marcel Dekker, 2000:393–411)

The present invention provides control of pH over the entire release phase by providing at least one buffering substance that can buffer the pH change immediately after exposure to an aqueous environment, and if necessary, at least one additional buffering substance which provides long term pH control as well as neutralization of any acidic polymer groups. This principle is applicable to starch microparticles coated with a film forming polymer, for example PLGA, and to microparticles consisting only of one biodegradable polymer, for example PLGA. The manufacture of such microparticles using emulsion systems, spray drying or spraying—freezing are known to a person skilled in the art and need not be described here.

The buffer substance, or buffer substances, can be incorporated by any means. They can be incorporated in the form of a buffer solution or in solid form, as particles, or as a combination.

The pH-sensitivity of the biologically active substance is important for the choice of the buffer substance, or combination of buffer substances, to be used. Although it is generally desirable to use only one buffer substance it will in many cases provide better stability of the biologically active substance to use at least two buffer substances, one primarily being able to control the pH immediately after injection for up to a few days and another being able to provide control of pH beyond the time point where the shorter acting buffering substance is no longer providing adequate pH control. In some cases more than one rapidly acting and/or long acting buffer substance is needed. In most cases it is possible to carry out preparatory trials to determine which buffer substance, or combination of buffer substances, to use. The simplest way is to assess the stability of the biologically active substance in vitro at different pH values, choose appropriate buffer substances and assess the stabilising effect of these on the biologically active substance. It is also possible to approach the choice of buffer substances from the known pH stability of the biologically active substance and from a general knowledge of the pH over time when certain predefined polymer compositions, for example certain polymers of PLGA, either in acidic form or neutralized, and buffer compositions are used. Such information, also showing how the pH changes with time, can be derived from the use of appropriate marker molecules, or combination of marker molecules, for example as described in Fu et al, Pharmaceutical Research 17(1) 2000, 100–106. This approach has the advantage that the information obtained is based on the complete formulation and therefore takes into account any combination effects and diffusion restrictions. Yet another approach to establish that the chosen buffers can provide adequate buffering can be obtained by in vitro release studies on the biologically active substance, including an assessment of the total recovery, or by determination of the pharmacokinetics, including bioavailability, after injection in experimental animal or man.

In the preparation of the core, buffer substances can be added to the starch solution or to the solution of the biologically active substance, or to the solution obtained after mixing of the starch solution with the solution or suspension of the biologically active substance. In both cases a buffer solution may be used or the buffer can also be added in particulate form. Obviously a combination, or combinations of a dissolved and undissolved buffer can also be used.

Buffer substances can also be added to the core in the drying step, by inclusion in the final washing solution. In this case the buffer is dissolved in the washing solution.

According to another alternative buffer substances can be added to the core by spraying, preferably using air suspension technology. The buffer substance, or buffer substances, can be applied as a buffer solution preferably in dissolved form or together with a polymer either in dissolved or particulate form, if for example, an improved adhesion between the core and the release regulating coating is needed. It is possible to use chemically neutral polymers. It is also possible to use polymers containing acidic groups, preferably then pre-neutralized, it being preferred to choose polymers which do not generate large amounts of acidic metabolites immediately after exposure to an aqueous environment, one example being PLGA with relatively high molecular weight with a composition providing a relatively slow biodegradation.

The buffer substance, or combination of buffer substances, can also be added to the coating solution or coating emulsion. When a coating emulsion is used it is preferred to include any water soluble, or highly water soluble, buffers in the water phase. Buffer substances added in particulate form can be added either to the organic or to the water phase of the coating emulsion. The amount of buffer substance needed to achieve the desired pH for the coating emulsion can be determined by measuring the pH of the aqueous phase of the emulsion. It is also possible to use non-buffer salts to modify the properties of the coating polymers.

In addition to the pH-sensitivity of the biologically active substance, the composition of the coating influences upon the amount and nature of the buffering substances to be used. When the coating consists of a high proportion of low molecular weight oligomers containing acidic end groups, more buffer is needed to control the pH within acceptable limits immediately, or shortly, after injection of the microparticles. Thus the amount, and optionally proportion, of rapidly acting buffer substances should generally be high. When the coating consists entirely of high molecular weight PLGA polymers the emphasis is on controlling the pH during the time period when the biodegradation of that polymer is intensive, which is normally some weeks or months after injection, and thus a high proportion and/or amount of slow acting buffer substances able to provide long lasting buffer control is to be used. Generally the nature and amount of buffer substances to be used can be adjusted between these two extremes.

Furthermore, it has also surprisingly been found that the initial rapid reduction of pH well before any significant degradation of e.g. PLGA takes place is due to the presence of water soluble acidic oligomers in the polymer that can rapidly diffuse to the microparticle core and reduce the interior pH with detrimental consequences for the encapsulated biologically active substance. In addition to providing recognition of this problem, thus enabling the proper choice of polymer, especially in connection with the pH stability profile of the biologically active substance and the selection of buffer substances employed in the formulation, the present invention further provides a means for reducing the harmful effects of water soluble acidic oligomers present in, for example commercially available polymers used to form microparticles or shells or coatings in the microparticles.

When relatively short durations of release of the biologically active substance is required, relatively low average molecular weight polymers are used to control the release kinetics of said encapsulated biologically active substance. Such polymers may contain free acidic end groups, as is the case for some PLG polymers, and the presence of such free carboxylic groups is often beneficial or required for controlling the release kinetics adequately. However, such polymers may also contain a fraction of oligomers which are sufficiently water soluble to be able to diffuse into the core or interior of a microparticle preparation when such a preparation is exposed to an aqueous environment, for example after parenteral administration. This is generally highly undesirable when the biologically active substance is sensitive to an acidic or low pH.

This invention therefore provides a means for reducing or eliminating such harmful oligomers from, for example, PLG polymers. Said means is based on the water solubility of these oligomers in that these are allowed to partition into water. It may be possible to obtain a sufficient reduction of the content of these acidic oligomers by extraction of the polymer, preferably in a form with a high surface are, for example as small particles, into a water phase. However, this is somewhat inefficient and unreliable process, and may leave too high residues of the oligomers in the polymer. It is preferred to use a process in which the polymer is dissolved and thus all oligomers can diffuse freely and are not trapped in, for example, inside small particles of the polymer. In the moste preferred approach for a polymer that is soluble in an organic solvent it is dissolved in an organic solvent which is able to form a two phase system with a water phase. This provides for an efficient removal of the water soluble oligomers to the water phase. The process can of course be repeated as many times as is necessary. If considered beneficial the phases can be separated by centrifugation, but often sedimentation is sufficiently rapid.

This procedure is especially convenient in connection with a process that utilises an emulsion in a coating step, for example an air suspension coatin process, as it is not necessary to dry the polymer, as otherwise would normally be tha case as some of these polymers hydrolyse in the presence of water, before using it in the process, but rather carry out the extraction step immediately before the coating.

Therefore, in summary, one embodiment of the invention is represented by the case where a polymer used in the manufacture of the microparticles, for instance the biocompatible and biodegradable polymer applied as a release-controlling shell, is chosen so as to contain, or has been purified so as to contain water-soluble oligomers below a level which is harmful to the biologically active substance used, Some preferable embodiments in connection with buffer substance(s) used according to the invention can be summarized as follows.

The buffer substance(s) is (are) preferably added in any one, or a combination, of steps a), b), e) or f).

Generally, the purpose of the buffer substance(s) is to prevent the pH value after exposure to an aqueous environment to fall below a level which is detrimental to the biologically active substance. A pH-limit of 3 is generally applicable in this respect. However, according to different embodiments said buffer substance(s) has (have) the ability of keeping the pH above 4, preferably above 5, more preferably above 6, for instance around 6,5.

Of course, it should also be noted that the pH should not either be caused to rise to such a high level which is detrimental to the substance in question. Generally this means that the pH should not be caused or allowed to rise above pH 10, preferably not above pH 9.

Another especially preferable embodiment is represented by the case where at least two buffer substances are added, one being able to control the pH immediately after said exposure of the microparticles to an aqueuous environment, and another being able to provide control of said pH after said first substance does not any longer provide adequate pH control. The most preferred embodiment is one in which there is some overlap of the buffering function of said buffer substances to ensure that the formulation is sufficiently buffered throughout the release phase.

Last-mentioned another buffer substance is preferably able to provide pH control for at least 6 hours, more preferably at least 12 hours, even more preferably at least one day and most preferably at least three days after said exposure.

In the case where a shell is used on the microparticles, said one buffer substance is preferably incorporated into the shell and said another buffer substance is preferably incorporated into the matrix or core of said microparticles.

However, according to another preferable embodiment said at least one buffer substance is applied onto the core before the shell is applied to the same. In other words, the buffer substance(s) will be present between core and shell in this embodiment.

Generally, the buffer substances to be used in connection with the invention are selected from substances which are previously known per se as buffering substances. Particularly interesting buffer substances are those which are suitable for parenteral administration, e.g. phosphate; arginine; histidine; salts of acids, for instance lactic and glycolic acids; carbonate, for instance zinc carbonate; oxide, for instance zinc oxide; and proteins, for instance human serum albumin.

Generally, the concentration of buffer substance(s) used in soluble form is 1–500 mM, preferably 5–250 mM and more preferably 10–100 mM, and in particulate form is 0.1–30%, preferably 0.5–20% and more preferably 1–12% (based on the weight of the core). The maximum amount that can be used as particulates is determined by the capability of the core and the coating to retain their beneficial properties.

The buffer substance to be used for a longer adequate pH control is preferably selected from phosphates, oxides, hydroxides and carbonates.

The buffer substance to be used for the pH control immediately after the exposure of the microparticles to said aqueous environment is preferably selected from zinc carbonate, zinc oxide, zinc hydroxide, zinc phosphate, zinc hydroxy carbonate, magnesium oxide, magnesium hydroxide, magnesium carbonate, magnesium trisilicate, calcium hydroxide, potassium carbonate, calcium phosphate, calcium hydroxide, calcium carbonate, sodium carbonate, aluminium hydroxide, basic aluminium carbonate, dihydroxyaluminium sodium carbonate, dihydroxyaluminium aminoacetate, ammonium phosphate and magaldrate.

When the produced microparticles are used, either they are coated with a release-controlling outer shell or not, and the dry microparticles are suspended in a suitable medium, specifically to permit injection. Such media and processes in these regards are well known within the field and will not need here to be described in further detail. The actual injection can be given through a suitable needle or with a needle-free injector. It is also possible to inject the microparticles using a dry powder injector, without prior resuspension in an injection medium.

Apart from the advantages which have been discussed above, the process according to the invention has the advantage that the yield of the biologically active substance is generally high, that it is possible to obtain a very high active substance content in the microparticles whilst retaining the bioactivity of the substance, that the obtained microparticles have the correct size distribution for use for parenteral, controlled (for example delayed or sustained) release, since they are too large to be phagocytized by macrophages and small enough to be injectable through small needles, for example 23G–25G, and that endogenic and neutral degradation products are formed upon degradation of the microparticles, by which means the active substance, for example, can be prevented from being exposed to an excessively low pH value. Moreover, the process itself is especially well suited to rigorous quality control.

The process according to the invention is especially interesting in connection with proteins, peptides, polypeptides, polynucleotides and polysaccharides or, in general, other drugs or biologically active substances which are sensitive to or unstable in, for example, organic solvents, primarily water-soluble substances. Recombinantly produced proteins are a very interesting group of biologically active substances. Generally speaking, however, the invention is not limited to the presence of such substances, since the inventive concept is applicable to any biologically active substance which can be used for parenteral administration. Apart from in connection with sensitivity or instability problems, the invention can thus also be of special interest in such cases where it would otherwise be difficult to remove solvent or where toxicological or other environmental problems might arise.

The biologically active substance can be used in different physical forms, as a solution or as a suspension, for example complexed to metals or precipitated with PEG or by other methods known in the art.

Classes of biologically active substances to be used are e.g. recombinant proteins, glycosylated recombinant proteins, pegylated recombinant proteins, growth factors, cytokines, blood coagulation factors, monoclonal antibodies, LHRH analogues, and vaccines.

Specific examples of substances are growth hormone, (e.g. human growth hormone and epidermal growth hormone) erythropoietin and analogues thereof, interferon ($\alpha$, $\beta$, $\gamma$), blood coagulation factors V–XIII, protein C, insulin and derivatives thereof, macrophage-colony-stimulating factor, granulocyte-colony-stimulating factor, interleukin, glucagon-like peptide 1 or 2, C-peptide, leptin, tumour necrosis factor and epidermal growth factor.

Usable biologically active substances of the non-protein drug type can be chosen from the following groups:

Antitumour agents, antibiotics, anti-inflammatory agents, antihistamines, sedatives, muscle-relaxants, antiepileptic agents, antidepressants, antiallergic agents, bronchodilators, cardiotonic agents, antiarrhythmic agents, vasodilators, antidiabetics, anticoagulants, haemostatic agents, narcotics and steroids.

According to another aspect of the invention, it also relates to novel microparticles of the type which are obtainable by means of the process according to the invention. The novel microparticles according to the invention are not limited, however, to those which can be produced by means of the said process, but comprise all microparticles of the type in question irrespective of the production methods.

More specifically, these are microparticles suitable for parenteral administration, preferably by way of injection, to a mammal, especially a human, and containing a biologically active substance, which microparticles consist substantially of starch that has an amylopectin content in excess of 85 percent by weight, of which at least 80 percent by weight has an average molecular weight in the range 10–1000 kDa, which have an amino acid content of less than 50 µg per dry weight of starch and which lack covalent chemical cross-linking between the starch molecules, and which microparticles contain at least one buffer substance having the ability of keeping the pH of the produced microparticles above 3 if exposing the microparticles to an aqueous environment, e.g. at injection into a mammal, including man.

The starch on which the microparticles in question are based is preferably one of the types of starch defined above in connection with the process.

According to a preferred embodiment of the microparticles according to the invention, the bioactivity of the biological substance in these is at least 80%, preferably at least 90% of the bioactivity that the substance exhibited before it was incorporated into the starch. The said bioactivity is most preferably largely retained or preserved in the microparticles.

Yet another preferred embodiment of the invention is represented by microparticles which are biodegradable in vitro in the presence of $\alpha$-amylase and/or amyloglucosidase.

Another embodiment is represented by those that are biodegradable and are eliminated from tissue after subcutaneous or intramuscular administration.

An especially preferred embodiment of the microparticles is represented by particles which have a release-controlling shell of at least one film-forming, biocompatible and biodegradable polymer.

The said polymer is preferably a homopolymer or copolymer made from $\alpha$-hydroxy acids, the said $\alpha$-hydroxy acid preferably being lactic acid and/or glycolic acid. Another variant is cyclic dimer of an $\alpha$-hydroxy acid which is preferably selected from the group consisting of glycolides and lactides.

Such polymers or dimers (of the PLGA type, for example) are precisely described in the prior art, and further details of these may therefore be obtained therefrom.

Another embodiment is represented by microparticles in which, in addition to said polymer, the shell contains at least one release regulating substance. Such a substance is preferably water soluble or sparingly water soluble. It is preferably selected from lactic acid, oligomers containing lactic acid and glycolic acid.

It may also advantageously be selected from substances comprising polyethylene glycol (PEG) and block copolymers comprising PEG as one of the blocks.

Another interesting embodiment is represented by microparticles which have an outer layer of at least one water soluble substance having the ability to prevent aggregation of the microparticles.

Furthermore, all preferable embodiments of the buffer substances which have been disclosed in connection with the process are of course applicable also to the microparticles per se. This for instance means that the buffer substance(s) has (have) the ability of keeping the pH above 4, preferably above 5, more preferably above 6, for instance around 6.5.

Preferred embodiment of the microparticles are also represented by those microparticles that are obtainable or are produced by means of a process as has been defined above, either in general or in the form of any preferred embodiment of the said process.

Some aspects of the invention in this context are represented by the following microparticles, or microparticle preparations.

Microparticles containing a biologically active substance, said substance being a recombinant protein that is present at a loading of at least 0.2% by weight, which microparticles contain at least one buffer substance having the ability of keeping the pH of the produced microparticles above 3 if exposing the microparticles to an aqueous environment, e.g. at injection into a mammal, including man.

Said recombinant protein is preferably present at a loading of at least 0.5% by weight, more preferably at least 1% by weight.

The microparticles referred to preferably contain less than 5% by weight, more preferably less than 2% by weight, and most preferably less than 1% by weight, of polyethyleneglycol (PEG).

According to another preferable embodiment the microparticles have a release in vivo during the first 24 hours that is less than 30%, preferably less than 20% and most preferably less than 10%, of the total release.

Said release is determined from a concentration-time curve in the form of the ratio between the area under the curve during said first 24 hours and the total are under the curve in question, which is a standard determination. Details thereabout can be found in PCT application PCT/SE01/02165, the disclosure of which is hereby incorporated by reference, as concerns the release determinations.

Microparticles can also be accomplished by the present invention, which contain a biologically active substance in a biocompatible and biodegradable polymer in general, wherein acidic groups in said polymer have been essentially, or completely, neutralised prior to being incorporated into said microparticles.

Furthermore, microparticles are claimed which contain a biologically active substance in a biocompatible and biodegradable polymer in general, said polymer comprising a homopolymer or copolymer containing α-hydroxy acid units, which microparticles contain at least one buffer substance having the ability of keeping the pH of the produced microparticles above 3 if exposing the microparticles to an aqueous environment, e.g. at injection into a mammal, including man, wherein there is essentially no accumulation of acid metabolites in the interior, or center, of the microparticles during biodegradation of said homopolymer or copolymer containing α-hydroxy acid units.

Other embodiments of microparticles of the invention are the following.

Microparticles in which the polymer(s) used has (have) an amino acid nitrogen content which is less than 50, preferably at most 20, more preferably at most 10, and most preferably at most 5, µg per g of dry polymer.

Microparticles which have a content of aggregates of biologically active substance below 0.2% by weight as prepared, preferably also after storage as a dry preparation in a refrigerator for at least 6, preferably at least 12, most preferably at least 24 months.

Microparticles which can be reconstituted for injection within 2 minutes, preferably within 1 minute, when using a diluent containing carboxy methyl cellulose.

Microparticles which are injectable through a 26 G needle at a concentration of less than 10% by weight.

Microparticles which provide detectable levels of the active substance in serum or plasma for at least 1 week, preferably at least 2 weeks, after parenteral administration.

Microparticles which provide a pharmacodynamic effect for at least 1 week, preferably at least 2 weeks, more preferably at least 3 weeks and most preferably at least 4 weeks.

As concerns the different microparticle aspects of the invention it can also be added that all embodiments previously presented in connection with the process of the present invention, or with the microparticles of the present invention, are applicable also to these aspects.

As regards the determination of the biological activity for the microparticles containing active substance, this must be carried out in a manner appropriate to each individual biological substance. Where the determination is effected in the form of animal trials, a certain quantity of the biologically active substance incorporated in the starch microparticles is injected, possibly after these microparticles have been previously enzymatically dissolved under mild conditions, and the biological response is compared with the response obtained after injection of a corresponding quantity of the same biologically active substance in a suitable solution. Where the evaluation is made in vitro, for example in test tubes or in cell culture, the biologically active substance is preferably made fully available before the evaluation by the starch microparticles being enzymatically dissolved under mild conditions, after which the activity is determined and compared with the activity for a control solution having the same concentration of the biologically active substance in question. In any event, the evaluation shall include any non-specific effects of the degradation products of the starch microparticles.

The invention will now be explained further with reference to the following non-limiting examples

EXAMPLES

Example 1

Procedure for Preparing Starch Microspheres

A solution (30%, 2.9 g) of highly branched sheared starch with an average molecular weight of about 530 kDa, is prepared in 6 mM Histidine buffer, pH 6.4. A solution of PEG (38%, 35 g, average molecular weight 20 kDa) in 6 mM Histidine buffer, pH 6.4, is prepared. When the starch solution has cooled to about 55° C. a solution of the biologically active substance (1%, 1 ml), in a buffer appropriate for the biologically active substance, for example 6 mM Histidine buffer, pH 6.4, is mixed with the starch solution. If it is of interest to determine the pH in the microsphere a fluorescent marker (for example, D1951, which contains fluorescein and tetramethylrhodamin coimmobilized on dextran with an average molecular weight of about 70 kDa, from Molecular Probes Inc, Leiden, The Netherlands) can be added; for example 0.1 ml of a 1.7% solution and mixed with the solution of the biologically active substance prior to mixing the solution of the biologically active substance with the starch solution. Thereafter the PEG-solution is added slowly for about 8.5 min under stirring. The obtained water-in-water emulsion is kept at 4° C. for 2 days with appropriate stirring and for about 6 hours at 37° C.

The microparticles are washed at least 3 times by centrifugation with an appropriate buffer, for example 6 mM Histidine buffer, pH 6.4, at room temperature and lyophilized.

Example 2

Procedure for Preparing Starch Microparticles Containing a Solid Buffer Substance The procedure described in Example 1 is repeated but zinc oxide is added to the starch solution (11%) final concentration) after cooling to about 55° C. and prior to mixing with the PEG-solution.

Example 3

Procedure for Preparing a Buffered Coating Emulsion of PLGA

A buffered coating emulsion is prepared by dissolving the PLGA in ethyl actetate; 30 g of RG502H and 10 g of RG756 (Boehringer Ingelheim) are dissolved in 626,67 g of ethylacetate—mixed with a buffer solution (1333 g of 10 mM sodium phosphate, pH 7.8) containing Tween 80 (0.80 g) using a phase ratio of water:ethylacetate of 2 and homogenized. The pH of the water phase of the coating emulsion is around above 7. A similar coating emulsion without the buffer can have a pH below 4.

Example 4

Coating of Starch Microparticles

A coating emulsion according to WO 97/14408 is applied on the starch microparticles prepared according to example 1 and containing a biologically active substance to obtain a shell of PLGA.

Example 5
Application of Buffer by Spraying onto the Starch Microparticles

Prior to the application of the coating emulsion according to Example 4 a solution of a buffer is sprayed on the starch microspheres; 67 g of starch microspheres prepared according to Example 1 is introduced into the coating chamber of an air suspension coating apparatus and 100 g of a solution of phosphate buffer (10 mM, pH 7.8) is sprayed on the starch microparticles. After that a coating of PLGA (40 g in total consisting of 30G RG502H and 10 g of RG756, Doehringer Ingelheim) are sprayed on the starch microspheres according to WO 97/14408.

Example 6
Measurement of pH in Microparticles

The in situ pH of the microparticles can be determined during in vitro release as follows:

Use a confocal microscope (Phoibos 100, Sarastro Inc, Stockholm, Sweden) with the software Image Space (Molecular Dynamics, Sunnyvlae, Calif.) with the following settings: 10× objective; excitation laser (488 nm, 5.1 mV), rad emission (580 nm), photomultplicator 870, green emission (525 nm), photomultplicator 870, beam splitter 560 nm, Subtract the dark values from the data before the quote pictures are made and then measure by selecting a rectangular area in the picture to read the 525/580 ratio. A suitable probe to use is fluorescein (FITS) and tetramethylrhodamin (TMR) coimmobilised on dextran (average molecular weight 70 kD) which can be obtained from, for example Molecular Probes. Other appropriate equipments and probes can be used.

Prepare a standard curve using the probes encapsulated in microparticles, for example starch microspheres, of the fluorescence emission 525/580 nm against the pH by adjusting the pH of the in vitro release buffer used by addition of HCl in the pH range 4,0 to 7.4. The standard curve obtained is essentially linear and can be used to determine the pH of the microsphere, or microcapsule, interior. A standard curve can also be prepared without having the probes encapsulated in microspheres but encapsulation is preferred.

Measure the the fluorescence emission 525/580 nm of the microparticle preparations to determine their pH.

Example 7
Determination of the pH Inside Microspheres

To illustrate the effect of buffering, microparticles preparations having the same composition of the coating (25% RG756 and 75% RG502H; Boehringer Ingelheim) were prepared according to Examples 1, 2 and 5. Preparation 1 only contained the buffer remaining after three centrifugation washes with histidine buffer (6 mM, pH 5.5) of the starch microspheres followed by lyophilization and subsequent coating. Preparation 2 was prepared as Preparation 1 except that prior to adding the coating by air suspension coating a pre-coat (100 ml, 10 mM phosphate, pH 7.4) was sprayed on to the starch microspheres. Preparation 3 was prepared as Preparation 1 except that zinc oxide (11%) was encapsulated in the starch microspheres according to Example 2.

The results are presented in FIG. 1, which shows pH versus time during the in vitro release referred to.

The same coating composition was used to enable comparison of the different approaches to control pH. With other compositions of the coating the actual pH values obtained may differ but the trend will remain the same. Preparation 1, which contained only some of the buffer used to wash the starch microspheres prior to coating, had a low pH during the first two days and thereafter a pH much closer to neutral. Preparation 2, to which additional buffer was added by spraying prior to application of the coating, had a pH much closer to neutral also during the first two days. Preparation 3, containing zinc oxide encapsulated in the starch microspheres, had a pH much closer to neutrality than Preparation 1 during the first two days of the in vitro release and thereafter a neutral pH up to day 5.

This experiment shows that unless additional buffering of starch microspheres coated with this mixture of these two PLGA polymers is done the pH during the initial period of release can fall to dangerously low levels. It should be noted that with another composition of the PLGA coating the initial pH could reach significantly lower levels and also that without using a chemically neutral polymer for the core the pH could be expected to drop even further. Both the addition of additional buffer substance by spraying prior to coating and encapsulation of additional buffer substance in the starch microspheres enable the pH to be kept at higher levels thus providing a less harmful microenvironment for an acid sensitive biologically active substance. This experiment also shows that at the time when significant PLGA hydrolysis is expected to start, at least two weeks after injection for this composition of the pH of the microparticle preparations are 6 or higher, that is close to neutrality.

Example 8
Procedure for Encapsulating a Recombinant Protein in Starch Microparticles The procedure from Example 2 is followed, with the following exceptions: the fluorescent probe is omitted; the microparticles are washed using a 6 mM Histidine buffer with pH 5.5; and 32 g of the PEG solution are used. The zinc oxide is mixed with the starch solution prior to adding the recombinant protein.

Example 9
Coating of Starch Microparticles Containing a Recombinant Protein

The procedure from Example 4 is repeated using a coating having a composition of 60% of RG 502 H and 40% of RG 503 (Boehringer Ingelheim). The RG 502 H polymer is a polymer with an acid number of 9 mg K OH/g. About 60 g of polymer dissolved in an oil-in-water coating emulsion, wherein ethyl acetate is used as an organic solvent, are applied onto 100 g of starch microspheres. 0.04% (w/w) of polysorbate 80 is used to stabilize the emulsion.

What is claimed is:

1. Microparticles containing a biologically active substance, wherein the microparticles consist essentially of starch having an amylopectin content exceeding 85% by weight, of which at least 80% by weight has an average molecular weight within the range of 10–10,000 kDa, and have an amino acid nitrogen content of less than 50 μg per gram dry weight of starch, and which have no covalent chemical cross-linking between the starch molecules, and wherein the microparticles contain at least one buffer substance having the ability of keeping the pH of the produced microparticles above 3 upon exposure to an aqueous environment.

2. Microparticles according to claim 1, in which the starch has a purity of at most 20 μg amino acid nitrogen per g dry weight starch.

3. Microparticles according to claim 1, in which the bioactivity of the biological substance is at least 80%, at least 90%, or essentially maintained compared with the bioactivity exhibited by the substance prior to its incorporation in the starch.

4. Microparticles according to claim 1, which are biodegradable in vitro in the presence of alpha-amylase and/or amyloglucosidase.

5. Microparticles according to claim 1, which are biodegradable and are eliminated from tissue after subcutaneous or intramuscular administration.

6. Microparticles according to claim 1, which have a release-controlling shell of at least one film-forming biocompatible and biodegradable polymer.

7. Microparticles according to claim 6, in which the polymer is a homopolymer or copolymer containing alpha-hydroxy acid units.

8. Microparticles according to claim 7, in which the alpha-hydroxy acid is lactic acid and/or glycolic acid.

9. Microparticles according to claim 6, in which said shell contains at least one release regulating substance, in addition to said polymer.

10. Microparticles according to claim 9, in which said substance is water soluble or sparingly water soluble.

11. Microparticles according to claim 10, in which said substance is selected from lactic acid, oligomers containing lactic acid and glycolic acid.

12. Microparticles according to claim 10, in which said substance comprises polyethylene glycol (PEG) or a block copolymer comprising PEG as one of the blocks.

13. Microparticles according to claim 6, wherein said at least one buffer substance is present between the particle core and its shell.

14. Microparticles according to claim 1, which are suitable for parenteral administration.

15. Microparticles according to claim 1, which have an outer layer of at least one water soluble substance having the ability to prevent aggregation of the microparticles.

16. Microparticles according to claim 1, which are injectable using a 23 G needle.

17. Microparticles according to claim 1, which are injectable using a 25 G needle.

18. Microparticles according to claim 1, which are injectable through the skin using a dry powder injection.

19. Microparticles according to claim 1, in which said at least one buffer substance has the ability of keeping said pH above 4, above 5 or above 6.

20. Microparticles according to claim 1, which contains at least two buffer substances, one being able to control the pH immediately after said exposure of the microparticles to an aqueous environment, and another being able to provide control of said pH at that point of time where said first substance does not any longer provide adequate pH control.

21. Microparticles according to claim 1, which have a content of aggregates of said biologically active substance below 0.2% by weight as prepared.

22. Microparticles according to claim 1, which can be reconstituted for injection within 2 minutes or within 1 minute, when using a diluent containing carboxy methyl cellulose.

23. Microparticles according to claim 1, which are injectable through a 26 G needle at a concentration of less than 10% by weight.

24. Microparticles according to claim 1, which provide detectable levels of the biologically active substance in serum or plasma for at least 1 week, or at least 2 weeks after parenteral administration.

25. Microparticles according to claim 1, which provide a pharmacodynamic effect for at least 1 week, at least 2 weeks, at least 3 weeks, or at least 4 weeks.

26. Microparticles according to claim 1, which contain at least one buffer substance as defined in claim 37.

27. Microparticles according to claim 1, which contain, as said biologically active substance, the biologically active substance selected from growth factors, insulin, erythropoietin, interferon α, interferon β, interferon γ, blood coagulation factors V, VI, VII, VIII, IX, X, XI, XII and XIII, protein C, glucagon-like peptide 1 or 2, C-peptide, vaccine, epidermal growth hormone, human growth hormone, LHRH-analogues, civamide, macrophage colony-stimulating factor, granulocyte colony-stimulating factor, leptin and interleukin, or an analogue or derivative of any one thereof, which possesses essentially the same pharmacological activity as the biologically active substance or improved pharmacological activity as compared thereto.

28. Microparticles according to claim 1, wherein the aqueous environment comprises an injection site in a mammal.

29. Microparticles according to claim 1, wherein the aqueous environment comprises an injection site in a human.

30. Microparticles according to claim 14, wherein the parental administration is via injection.

31. Microparticles according to claim 30, wherein the injection is in a mammal.

32. Microparticles according to claim 30, wherein the injection is in a human.

33. Microparticles according to claim 20, wherein said at least two buffer substances have overlapping buffering functions.

34. Microparticles according to claim 21, wherein said content of aggregates of said biologically active substance is below 0.2% by weight after storage as a dry preparation in a refrigerator for a time period selected from the group consisting of at least 6 months, at least 12 months, and at least 24 months.

* * * * *